United States Patent

Bardenheuer et al.

[11] 4,102,197
[45] Jul. 25, 1978

[54] SAMPLING MOLTEN STEEL

[75] Inventors: Friedrich Bardenheuer, Krefeld, Germany; Gustav Kolb, 5984 Garbeck, Germany

[73] Assignees: Mannesmann Aktiengesellschaft, Dusseldorf; Gustav Kolb, Garbeck, both of Germany; part interest to each

[21] Appl. No.: 775,160

[22] Filed: Mar. 7, 1977

[30] Foreign Application Priority Data

Mar. 8, 1976 [DE] Fed. Rep. of Germany ....... 2609945

[51] Int. Cl.$^2$ ............................................. G01N 1/12
[52] U.S. Cl. ................................. 73/354; 73/DIG. 9
[58] Field of Search .................. 73/425.4 R, DIG. 9, 73/354; 164/4; 249/DIG. 4

[56] References Cited

U.S. PATENT DOCUMENTS

| 3,367,189 | 2/1968 | Curry | 73/DIG. 9 |
| 3,481,201 | 12/1969 | Falk | 73/DIG. 9 |
| 3,685,359 | 8/1972 | Boron | 73/DIG. 9 |
| 4,007,641 | 2/1977 | Kelsey | 73/DIG. 9 |

FOREIGN PATENT DOCUMENTS 6,804,930  5/1968  Netherlands .................... 73/DIG. 9

Primary Examiner—S. Clement Swisher
Attorney, Agent, or Firm—Ralf H. Siegemund

[57] ABSTRACT

A single piece ceramic body has an inlet chamber, an inlet duct and a disc-shaped cavity, that latter cavity is, as far as the body is concerned, of open construction but the opening is closed by a plug. That plug may contain one or two thermo elements, and the inlet chamber may be constructed as an opening with a partitioning sheet or as a duct system with a lateral port and a slag trapping dome. The mold cavity has also venting opening.

15 Claims, 7 Drawing Figures

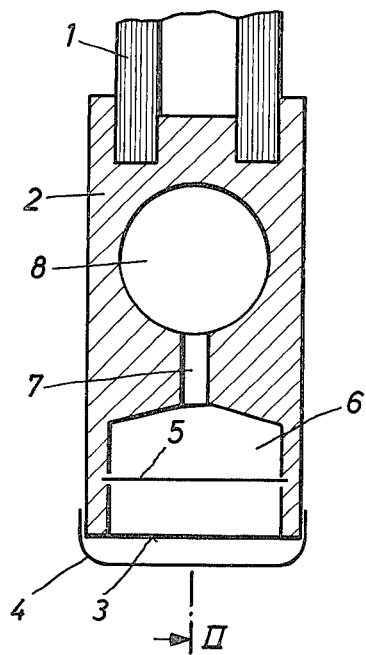
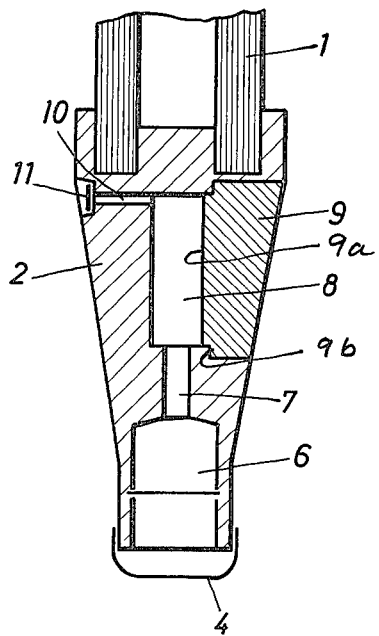
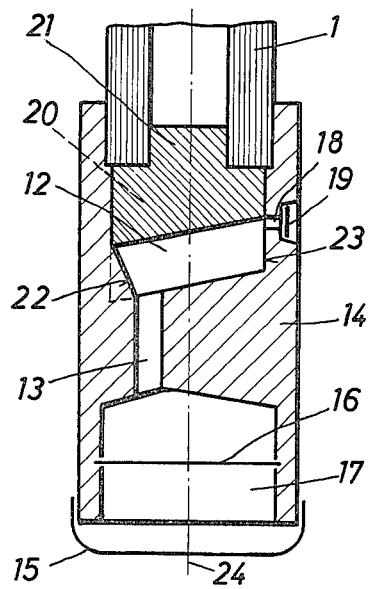

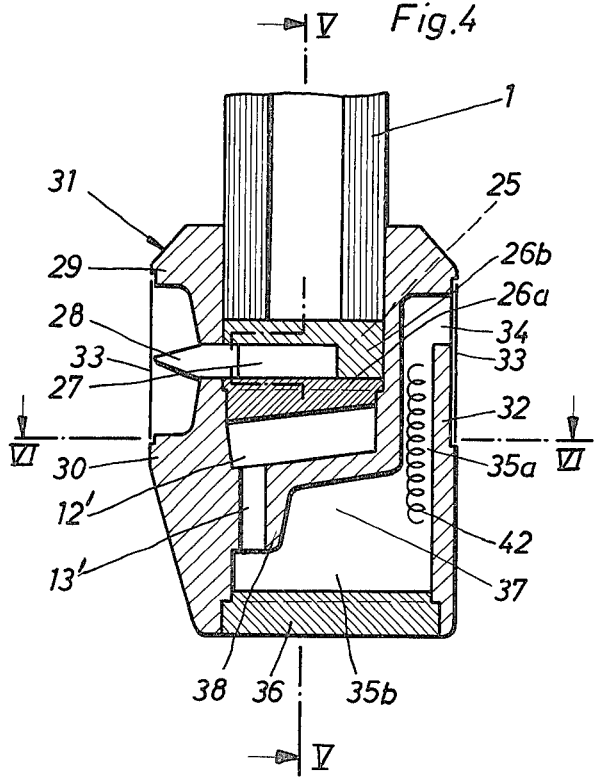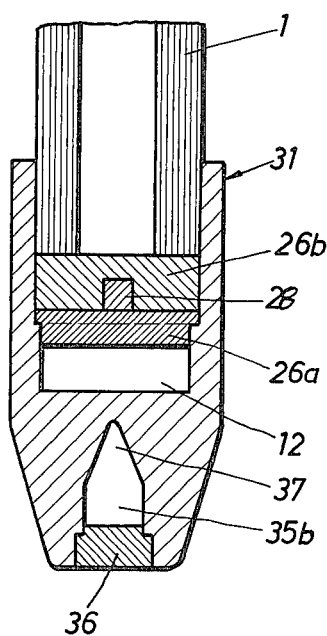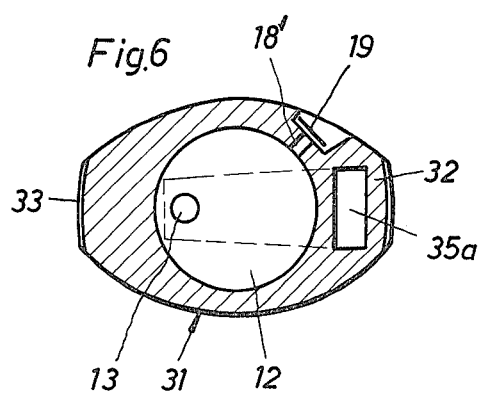

SAMPLING MOLTEN STEEL

BACKGROUND OF THE INVENTION

The present invention relates to a ceramic sampler for liquid steel.

Sampling devices or probes for extracting a sample of molten steel from a steel bath are usually constructed as small molds with entrance ducts, openings or the like, and a mold cavity to be filled with steel as the sampler is dipped into the steel bath. The term liquid or molten steel or steel bath is to be understood in a rather wide sense; it is to include, e.g., cast iron melts as well as the content of a blowing steel converter.

Sampling devices of the type referred to above generally, and of known construction, include a cardboard pipe as a holder tube, which containes a two-part mold made of metal and a quartz tube. The mold cavity has the complementary configuration of a disc, i.e., of a flat cylinder. This disc is integral with a pin corresponding to the inlet duct for the mold cavity through which the sampled steel entered the cavity. The disc is usually used for spectrum analysis and the pin for a gas analysis. Hence, the inlet duct is really also part of the mold cavity. This mold is held in the holder tube by a rather easily destructible tube of bound sand and a ceramic front disc. This latter tube has been shifted into a thin wall cardboard tube and bonded thereto. In total, the sampler consists of six distinct parts.

Other sampling devices are known (German Patent No. 2,126,501) which is not quite suited for taking a laboratory type sample, but are used to determine specifically the carbon content of a blowing converter. The geometry of this sampler is not very significant but the device has to carry two temperature sensing elements. This known ceramic sampler has also a two part mold. Just the tooling for making these two different parts is quite expensive. In order to simplify the making of these parts one could divide the mold in longitudinal direction; however, the mold inevitably undergoes a thermal shock when immersed in the steel bath so that dross and slip forms and crystallization water is released which endangers the bondage between the two mold parts because forces act upon them towards separation.

DESCRIPTION OF THE INVENTION

It is an object of the present invention to provide a new and improved steel sampling device which is of simpler construction and avoids the various deficiencies outlined above.

It is a particular object of the present invention to improve on ceramic mold type steel samplers, whereby particularly the sampling device should permit employment of thermo feelers, but that aspect should not act as a limitation on the construction principles.

In accordance with the preferred embodiment of the present invention, it is suggested to provide a sample device as a single piece body having, basically two external openings. One opening leads via an inlet duct to the mold cavity proper, being of disc-shaped configuration and being located right at the other opening. That other opening is closed by a stopper whose innermost surface defines one of the two flat cavity surfaces.

The stopper is also made of ceramic and fastened to the main body through ceramic slip, but surfaces so fastened are relatively small and not subject to external forces tending to pry the mold open. The mold body is, in addition provided with a venting duct which is closed by a cover which will disintegrate in the molten steel. The duct should extend laterally and not vent into the holder tube (as in the case in prior art samplers). This cover is needed because the venting duct must not be too narrow as it must not be clogged, but sampled steel should not enter from the outside.

As regards the construction and location of the mold body and its cavities, basically two versions are proposed, having to do with the mutual orientation of the openings and of the mold cavity. In one version, the opening closed by the stopper is laterally oriented and the disc molding cavity has an upright orientation (i.e. the cylinder axis extends horizontally for a vertical direction of immersion). In a second version, the disc molding cavity extends generally horizontally and the stopper is affixed from above at the jointure with the holder tube. The cavity should, however, be slightly oblique to establish a low point inlet (where the inlet duct enters), and a high point for the venting duct.

The entrance chamber for the mold, being also one of the openings and leading to the inlet duct, is either at the bottom or to the side. In either case, it is closed by sheet metal covering which melts on contact with the steel.

Th those cases requiring concurrent temperature measurements, the stopper should serve as holder for the thermo feeler or feelers.

If the device is to be used for sampling a blowing converter, the inlet path for the steel must be constructed to permit quieting of the steel prior to entering the mold. Also, that inlet path must be constructed to collect and trap slag. Accordingly, the entire inlet duct path is of U-shaped configuration, of which one leg is the duct for molding the sample pin, while the other leg contains, e.g., an aluminum coil for quieting the steel. The transverse bottom of that U-configuration is enlarged to an inverted V-shaped dome separated from the inlet duct by a weir. The same construction can be used just for carbon content determination through temperature measurement inside of the mold by means of two thermo elements in the stopper.

DESCRIPTION OF THE DRAWINGS

While the specification concludes with claims particularly pointing out and distinctly claiming the subject matter which is regarded as the invention, it is believed that the invention, the objects and features of the invention and further objects, features and advantages thereof will be better understood from the following description taken in connection with the accompanying drawings in which:

FIG. 1 is a longitudinal section view through a new steel sampling device including an upright mold cavity for taking a sample from a quiet steel bath;

FIG. 2 is a section view along lines II—II of FIG. 1;

FIG. 3 is a longitudinal section view of a modified sampling device with a generally sideways oriented mold cavity;

FIG. 4 is a longitudinal section view of a device for taking a laboratory test sample from a blowing converter; and FIGS. 5 and 6 are respectively views along lines V—V and VI—VI in FIG. 4.

Proceeding now to the detailed description of the drawings, FIG. 1 shows a cardboard tube 1 and holder to which is affixed a sampling device which is basically comprised of a single piece body 2, made of ceramic material. The body 2 is constructed as a mold having an entrance of inlet chamber 6 with an opening 3 and communicating with a duct 7, which leads to a mold cavity 8.

Figure 7:
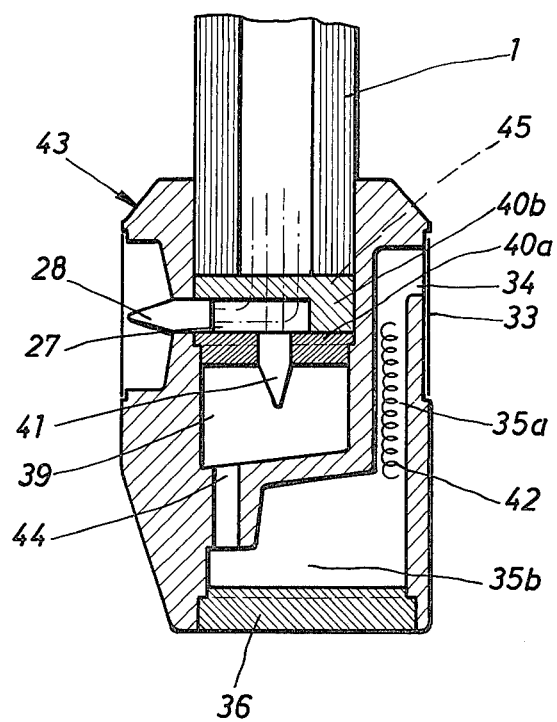
FIG. 7 is a longitudinal section view of a sampling device for sampling a blowing converter to determine the carbon content.

The opening 3 of chamber 6 is covered by a sheet metal cap or cover 4. The charge and inlet chamber 6 is divided or partitioned by a sheet metal disc 5. The duct 7 is, in effect, the mold cavity for the pin type sample to be used for gas analysis, and the mold cavity 8 has a contour for forming and molding a disc, i.e. a flat round cylinder. The disc molding cavity 8 has an upright orientation.

As can readily be seen, the body 2 does not have any joint or partitioning plane in the horizontal or in the vertical. The body 2 is, however, laterally of open construction or configuration, so that the cavity 8 is part of an opening extending basically over the one flat end face of mold cavity, and being closed by a stopper or plug 9. The plug 9 completes the mold in that its inner face 9a constitutes the mold side wall proper for that one end face of the disc to be made. Thus, the end face 9a of plug 9 has a diameter equal to the diameter of the cylindrical mold cavity 8. The stopper or plug 9 has a shoulder 9b to improve sealing, resetting or a stepwise enlargement of the opening which becomes the mold cavity to the extent not occupied by stopper or plug 9.

In addition to the several openings and cavities, body 2 is provided with a venting duct 10 which is stepwise enlarged as it leads from an upper portion of cavity 2 towards the outside. The one step enlargement establishes a shoulder against which abuts a covering wafer 11 made of cardboard.

The stopper or plug 9 is fastened to the respective opening of body 2 through ceramic slip or slop. It can readily be seen that the bonding surfaces involved are not subjected to external forces. Also, the shoulder 9a is quite small.

Turning now to FIG. 3, the sampling device connected to tube 1 is again a unitary or single piece body 14, having an inlet chamber 17 with a metal cover 15 and a partition 16. All these parts except the inner bottom of chamber 17, are completely round and of rotational symmetry with respect to an axis 24 being also the axis of tube 1. Quite importantly, the outer surface of body 14 is of round cylindrical configuration. This latter aspect is a first differentiating feature as between FIG. 3 and FIGS. 1 and 2.

The mold cavity 12 is flat-obliquely positioned in FIG. 3, and the inlet duct 13 is excentrically positioned, extending vertically but obliquely to cavity 12. Particularly, duct 13 leads into cavity 12 at the lowest point thereof, to make sure, that gas bubbles are not trapped in the cavity.

The oblique disposition of cavity 12 has its primary objective the avoiding of such a trap forming cavity portion. It should be noted that duct 7 leads also to the lowest point of cavity 8 in FIGS. 1 and 2. Analogously, a venting duct 18 in FIG. 3 leads to the uppermost zone of cavity 12. Duct 18 has also a stepwise enlargement which forms a shoulder, and a closing disc 19 rests against that shoulder.

The upper surface of the mold cavity is again defined by the inner round (oval) and flat surface of a stopper of plug 21. The plug sits in a cylindrical continuation chamber 20 of a bore of body 14, of slightly larger diameter of the bore which receives tube 1. Stopper 21 is, in addition, provided with an annular recess on which sits the inside end of tube 1. This way, tube 1 acts as a sealer of the joint between body 14 and stopper 21, thereby participates in sealing chambers 12 and 20.

With stopper 21 removed, mold cavity chambers 12 is clearly a continuation of cylindrical bore and chamber 20 has an oblique and, therefor, slightly oval bottom. The stopper or plug 21 has a similarly obliquely oriented and, therefor, slightly oval end face which defines one side of disc-shaped cavity 12 and completes the same accordingly. An obliquely portioned surface portion 22 makes sure that duct 13 does, in fact, lead to the lowest mold cavity point.

It should be emphasized that 22 and surface poriton 23 do not denote a single conical surface. The oblique portion 22 is provided only where shown and leading to duct 13, and 23 is a cylindrical surface portion defining bore or chamber 20 as continued in the mold cavity, and defines, therefor, a cylindrical mold cavity wall that is symmetric to and around axis 24. The mold cavity and the disc to be molded is, therefor, like an obliquely taken slice of a cylinder, except that at one point (namely 22) a cut, so to speak, is made in the opposite direction. Also, except for the detent as produced by portion 22, the resulting disc will have a cylindrical surface but with a cylindrical axis that is obliquely oriented to any normal direction on either of the flat sides of that disc. The detent produced at the surface portion 22 facilitates later clamping or holding of the disc in the laboratory test equipment.

The sampling device shown in FIGS. 4, 5 and 6 is constructed for sampling a blowing converter. The device differs generally from these previously described by the provision of a thermo element for measuring the steel bath temperature during sampling. Additionally, the inlet path of the sampling body is constructed for quieting the steel that enters the mold cavity. It is necessary for obtaining a representative reading to measure the temperature in the instant of sampling. Furthermore, the steel has quite a low viscosity during converter blowing, and contains gas to an extensive degree so that some treatment of the steel prior to entering the mold cavity is necessary.

The sampling device of FIGS. 4 to 6 is to be considered an evolution of the device shown in FIG. 3, as far as the overall geometry of the mold cavity is concerned. In particular, the mold cavity 12' proper for the sample disc is obliquely positioned and the feed duct 13' is correspondingly obliquely and excentrically oriented thereto. Thus, these two cavities 12' and 13' correspond to cavities 12 and 13 in material and general orientation and contour; the resulting samples are identical in shape.

The sampling devivce of FIGS. 4 to 6 has, however, a somewhat larger upper chamber 25 in a single piece body 31, receiving a multiple part stopper or plug. The lower plug part 26a is much shorter than stopper 21 of FIG. 3, but its one round (oval) surface defines also here the upper surface of the sampling mold cavity 12'.

Stopper or plug part 26a has an upper flange which rests on a shoulder of opening 25. The second stopper part 26b sits on part 26a and has a recess 27 which receives a thermo element 28. Thermo feeler 28 can slide on the upper surface of stopper part 26a. This way, element 28 can be slid in or out of the recess 27. For example, the thermo element 28 is placed completely into the recess while the body 31, the tube 1, and the plug 26a, 26b are being assembled. When in place, element 28 is pulled out by tweezers to some extent into the illustrated position in which the feeler tip is exposed to and reaches into the environ of the device. The electrical wires (not shown) lead from element 28 into the tube 1.

The temperature sensing tip of element 28 is located in a recess which is established by an upper barrier or bead 29, and a lower barrier or bead 30. These barriers protect the thermo feeler or element and particularly its tip when the device dips into the simmering bath of steel and slag.

As can be seen from FIG. 6, the device has also a venting duct 18' closed by a little disc 19. An overall protrusion 32 is provided opposite the area of thermo element 28, so that the overall, outer cross-section of the sampling body 31 is of somewhat overall contour; the beads 29 and 30 are included in that contour in the upper and central portion of the body 31. The portion 32 is provided with an lateral entrance port or opening 34 which continues in a vertical duct 35a. Opening 34 as well as the chamber of thermo element 28 are enveloped by a thin sheet metal sleeve 33, which melts as the sampler dips into the molten steel.

The downwardly extending ducts 35a contain an aluminum spiral 42 and continues horzontally in a transverse duct 35a, whose upper portion is enlarged into a dome 37 for collecting any slag. Dome 37 is quite high as slag must not be permitted to clog duct 13', being an upward continuation of duct 35b. These ducts 35a, 35b and 13' are, hydro (ferro-) dynamically speaking, a U-system.

The horizontal duct 35b as such is actually completed by a flat stopper with a shoulder or flange for being seated on a complementary shoulder in body 31. Reference numeral 38 refers to baffle, apron or weir between dome 37 and duct 13'. The dome itself has an inverted V or roof-shaped contour which is of advantage for trapping slag. These last two features are important so that later, upon destroying the device, ceramic parts are not clamped between steel parts, there are no parallel clamping surfaces.

The device shown in FIG. 7 is not used for actually obtaining a lab test sample, because the sample obtained is more or less useless after solidifcation. The device is to be used for temperature measurement during solidification. However, this difference in final result and purpose does not require any significant change of, for example, the construciton principles and details underlying FIGS. 4, 5 and 6. The main difference is the overall-shape of "mold" cavity 39, which is larger in axial direction, but has a similar diameter as cavity 12'. Also, a stopper or plug part 40b is quite similar to the stopper or plug part 26b of FIGS. 4 and 5, and recess 27 and thermo element 28 are similar accordingly.

The lower stopper or plug part 40a has diameter similar to the diameter of stopper of plug part 26a, but 40a does not have to have an oblique surface parallel to the bottom of cavity 39. Moreover, stopper or plug part 40a contains a second thermo element 41 whose sensing tip reaches into cavity 39. All other parts, ducts, cavities, etc., are similar in FIGS. 4, 5 and 7. Of course, there is one additional pair of electrical conductors, which pass through plug or stopper 40b into tube 1.

After having described three different sampling devices, all of which being constructed in accordance with the same basic principle underlying the invention, specific use of the device will be described next.

The sampling device of FIGS. 1 and 2 is handled as is conventional for steel bath samplers. As the body 2 dips into the molten steel, sheet cover 4 melts and steel enters opening 3. Aluminum parts may be placed between opening 3 and partition 5 to quiet the steel, if necessary. Partition 5 melts also and the steel flows into and through duct 7, into cavity 8. It is quite significant that cover 4 melts faster than cardboard disc 11 burns away. This disc 11 should burn relatively slowly, so that as the steel enters the upper part of entrance chamber 6, a slight excess pressure will push what is left of disc 11 out of the recess.

After the steel has filled cavity 8, steel will flow into venting duct 10. This steel pertains basically to the advanced portion of the flow and will, thus, solidify in duct 10 before the steel in cavity 8 has begun to solidify.

The operation of the sampler shown in FIG. 3 is quite similar, only the resulting molded body is different due to the different configuration and orientation of cavity and duct for lab sample and gas analysis, respectively. Also, the device of FIG. 3 is somewhat simpler to make.

The samples obtained with devices of FIGS. 4, 5 and 6 are similar to those obtained with the sampler of FIG. 3. Particularly, the timing considerations as between melting of sleeve 33 and burning of cover 19, are the same. As stated, the device of FIGS. 4–6 is used for sampling a blowing converter. The steel has a temperature of about 1600° C and has, therefor, very low viscosity. It attacks readily and vigorously the aluminum coil 42, and slag formed thereby as well as slag that enters from the outside is trapped in dome 37. The clean and quieted steel passes around weir 38 and enters duct 13' for passage into cavity 12'. After the several cavities have filled, steel in duct 18' will solidify first. The operation of the sampler as per FIG. 7, is the same, but is used differently as was mentioned earlier.

A modification of the devices as described, is for example, constituted by combining two samplers as per FIGS. 4 to 6 and FIG. 7 in a single piece structure with two U-duct systems, and two cavities.

The invention is not limited to the embodiments described above but all changes and modifications thereof not constituting departures from the spirit and scope of the invention are intended to be included.

We claim:

1. A ceramic sampling device for sampling molten steel, comprising:

a single piece body having an entrance chamber, an inlet duct extending from the chamber to a mold cavity of disc-shaped configuration, but being defined by an open configuration of the body, the body further including a venting duct and destructible means for closing the venting duct; and a stopper inserted into and affixed to the body at said open configuration and providing a mold-completing surface as to one flat side of the disc, said stopper and mold completing surface having a diameter equal to the diameter of the disc.

2. A sampling device as in claim 1, wherein the inlet duct leads into a low point of the mold cavity, the venting duct leads from a high point in the mold cavity, the body having means for connection to a tubular holder, the venting duct having an exit off the means for means for connection so that venting does not occur into the interior of the tubular holder when connected.

3. A ceramic sampling device for sampling molten steel, comprising:

a single piece body constructed in its upper part for connection to a tubular holder and having an entrance chamber, an inlet duct extending from the chamber to a mold cavity of disc-shaped configuration, upright orientation and being further defined by an open, laterally oriented configuration of the body, the body including a venting duct with an exit offset from the upper art so that venting will occur outside of the interior of the tubular holder when connected to the body;

destructible means for closing the venting duct; and a ceramic stopper inserted into and affixed to the body at said open configuration and providing an upright mold-completing surface as to one flat side of the disc, said stopper and mold completing surface having a diameter equal to the diameter of the disc.

4. A ceramic sampling device for sampling molten steel, comprising:

a single piece body constructed in its upper part for connection to a tubular holder and having an entrance chamber, an inlet duct extending from the chamber to a mold cavity of flat disc-shaped configuration, being oriented essentially transversally to the duct, but being defined by an open configuration of the body at its upper part;

the body including a venting duct with an exit offest from the upper art so that venting will occur outside of the interior of the tubular holder when connected to the body; and a ceramic stopper inserted into and affixed to the body at said open configuration from the top and providing a moldcompleting surface as to one flat side of the disc, said stopper and mold completing surface having a diameter equal to the diameter of the disc.

5. A sampling device as in claim 4, said disc-shaped mold cavity having an oblique position relative to a vertical axis, but being centrally oriented to said axis and having a peripheral surface being of cylindrical configuration relative to said axis.

6. A sampling device as in claim 5, said inlet duct being disposed excentrical to said axis, said peripheral surface portion having an oblique portion adjacent to the duct.

7. A sampling device as in claim 1, said entrance chamber being at the bottom of the body, there being at least one sheet metal closure in or at said chamber.

8. A sampling device as in claim 1, said stopper including at least one thermo sensing element.

9. A sampling device as in claim 8, said thermo sensing element projecting into the mold cavity.

10. A sampling device as in claim 8, said stopper having a recess receiving the thermo sensing element, being exposed to the exterior of the body.

11. A ceramic sampling device for sampling molten steel, comprising:

a single piece body having an entrance chamber, an inlet duct extending from the chamber to a mold cavity of disc-shaped configuration, but being defined by an open configuration of the body, said inlet duct and said entrance chamber forming a U-shaped duct system, the entrance chamber having a lateral entrance part off one of the legs of the U; and a stopper inserted into and affixed to the body at said open configuration and providing a mold-completing surface as to one flat side of the disc, said stopper and mold completing surface having a diameter equal to the diameter of the disc.

12. A sampling device as in claim 11, said U-shaped duct system being as to its transverse section closed by an additional stopper.

13. A sampling device as in claim 11, said U-shaped duct system having a transverse section being enlarged to form a slag trapping dome.

14. A sampling device as in claim 11, said dome being of inverse V-shaped contour.

15. A sampling device as in claim 11, the body including a laterally extending venting duct and destructible means for closing the venting duct.

* * * * *